United States Patent
Laaksonen et al.

(10) Patent No.: US 11,282,192 B2
(45) Date of Patent: Mar. 22, 2022

(54) TRAINING DEEP LEARNING ENGINES FOR RADIOTHERAPY TREATMENT PLANNING

(71) Applicant: Varian Medical Systems International AG, Palo Alto, CA (US)

(72) Inventors: Hannu Mikael Laaksonen, Espoo (FI); Janne Nord, Espoo (FI); Sami Petri Perttu, Helsinki (FI)

(73) Assignee: VARIAN MEDICAL SYSTEMS INTERNATIONAL AG

( * ) Notice: Subject to any disclaimer, the term of this patent is extended or adjusted under 35 U.S.C. 154(b) by 137 days.

(21) Appl. No.: 16/721,876

(22) Filed: Dec. 19, 2019

(65) Prior Publication Data

US 2021/0192719 A1 Jun. 24, 2021

(51) Int. Cl.
| | |
|---|---|
| *G06K 9/00* | (2006.01) |
| *G06T 7/00* | (2017.01) |
| *G06T 7/11* | (2017.01) |
| *A61N 5/10* | (2006.01) |

(52) U.S. Cl.
CPC .......... *G06T 7/0012* (2013.01); *A61N 5/1031* (2013.01); *G06T 7/11* (2017.01); *G06T 2207/20081* (2013.01); *G06T 2207/20084* (2013.01); *G06T 2207/30096* (2013.01)

(58) Field of Classification Search
CPC ..................... G06T 7/0012; G06T 7/11; G06T 2207/20081; G06T 2207/20084; G06T 2207/30096; A61N 5/1031; G06N 3/0472; G06N 3/0445; G06N 3/084; G06N 3/0454
USPC ........................................................ 382/159
See application file for complete search history.

(56) References Cited

U.S. PATENT DOCUMENTS

| | | | | |
|---|---|---|---|---|
| 2018/0144243 | A1* | 5/2018 | Hsieh | ............... G06F 11/30 |
| 2018/0315398 | A1* | 11/2018 | Kaul | ............. G06F 9/30014 |
| 2019/0180443 | A1* | 6/2019 | Xue | ............... G06K 9/6209 |
| 2020/0342359 | A1* | 10/2020 | Hu | ............... G16H 50/20 |
| 2020/0380367 | A1* | 12/2020 | Gupta | ............... G06K 9/6259 |
| 2021/0056412 | A1* | 2/2021 | Jung | ............... G06N 3/0445 |

(Continued)

OTHER PUBLICATIONS

Qi Dou et al., "3D Deeply Supervised Network for Automated Segmentation of Volumetric Medical Images", Medical mage Analysis, May 8, 2017, pp. 40-54, vol. 41 (Year: 2017).*

(Continued)

*Primary Examiner* — Van D Huynh
(74) *Attorney, Agent, or Firm* — Su IP Consulting

(57) ABSTRACT

Example methods and systems for training deep learning engines for radiotherapy treatment planning are provided. One example method may comprise: obtaining a set of training data that includes unlabeled training data and labeled training data; and configuring a deep learning engine to include (a) a primary network and (b) a deep supervision network that branches off from the primary network. The method may further comprise: training the deep learning engine to perform the radiotherapy treatment planning task by processing training data instance to generate (a) primary output data and (b) deep supervision output data; and updating weight data associated with at least some of the multiple processing layers based on the primary output data and/or the deep supervision output data. The deep supervision network may be pruned prior to applying the primary network to perform the radiotherapy treatment planning task for a patient.

18 Claims, 9 Drawing Sheets

(56) References Cited

U.S. PATENT DOCUMENTS

2021/0089861 A1* 3/2021 Sibille .................. G06K 9/6271
2021/0142168 A1* 5/2021 Kushnir ................. G06N 3/084

OTHER PUBLICATIONS

Veronika Cheplygina et al., "Not-so-supervised: a survey of semi-supervised, multi-instance, and transfer learning in medical image analysis", Article in Medical Image Analysis, Apr. 17, 2018, 19 pages.

International Search Report and Written Opinion of the International Searching Authority, International application No. PCT/EP2020/086250, dated Apr. 6, 2021.

Qi Dou et al., "3D Deeply Supervised Network for Automated Segmentation of Volumetric Medical Images", Medical Image Analysis, May 8, 2017, pp. 40-54, vol. 41.

Bo Wang et al., "Automated Prostate Segmentation of Volumetric CT Images Using 3D Deeply Supervised Dilated FCN", Proc. of SPIE, Mar. 15, 2019, pp. 109492S-1-109492S-8, vol. 10949.

Yang Lei et al., "Ultrasound Prostate Segmentation Based on 3D V-Net with Deep Supervision", Proc. of SPIE, Mar. 15, 2019, pp. 109550V-1-109550V-7, vol. 10955.

Xue Dong et al., "Synthetic MRI-aided Multi-organ Segmentation on Male Pelvic CT Using Cycle Consistent Deep Attention Network", Radiotherapy and Oncology, Elsevier, Oct. 17, 2019, pp. 192-199, vol. 141.

Yuyin Zhou et al., "Semi-Supervised 3D Abdominal Multi-Organ Segmentation via Deep Multi-Planar Co-Training", 2019 IEEE Winter Conference on Applications of Computer Vision, Jan. 7, 2019, pp. 121-140.

Dong Nie et al., "ASDNet: Attention Based Semi-supervised Deep Networks for Medical Image Segmentation", MICCAI 2018, LNCS 11073, 2018, pp. 370-378.

* cited by examiner

TRAINING DEEP LEARNING ENGINES FOR RADIOTHERAPY TREATMENT PLANNING

BACKGROUND

Radiotherapy is an important part of a treatment for reducing or eliminating unwanted tumors from patients. Unfortunately, applied radiation does not inherently discriminate between an unwanted tumor and any proximal healthy structures such as organs, etc. This necessitates careful administration to restrict the radiation to the tumor (i.e., target). Ideally, the goal is to deliver a lethal or curative radiation dose to the tumor, while maintaining an acceptable dose level in the proximal healthy structures. However, to achieve this goal, conventional radiotherapy treatment planning may be time and labor intensive.

SUMMARY

According to examples of the present disclosure, methods and systems for training deep learning engines for radiotherapy treatment planning are provided. One example method may comprise: obtaining a set of training data that includes unlabeled training data and labeled training data associated with a radiotherapy treatment planning task; and configuring a deep learning engine to include (a) a primary network that includes multiple processing layers and (b) a deep supervision network that branches off from the primary network at a checkpoint that is interposed between two processing layers.

The example method may also comprise: training the deep learning engine to perform the radiotherapy treatment planning task by processing training data instance to generate (a) primary output data using the primary network and (b) deep supervision output data using the deep supervision network. The deep supervision output data may identify anatomical feature(s) associated with the training data instance. The example method may further comprise: updating weight data associated with at least some of the multiple processing layers based on the primary output data or the deep supervision output data, or both.

DETAILED DESCRIPTION

The technical details set forth in the following description enable a person skilled in the art to implement one or more embodiments of the present disclosure.

Figure 1:
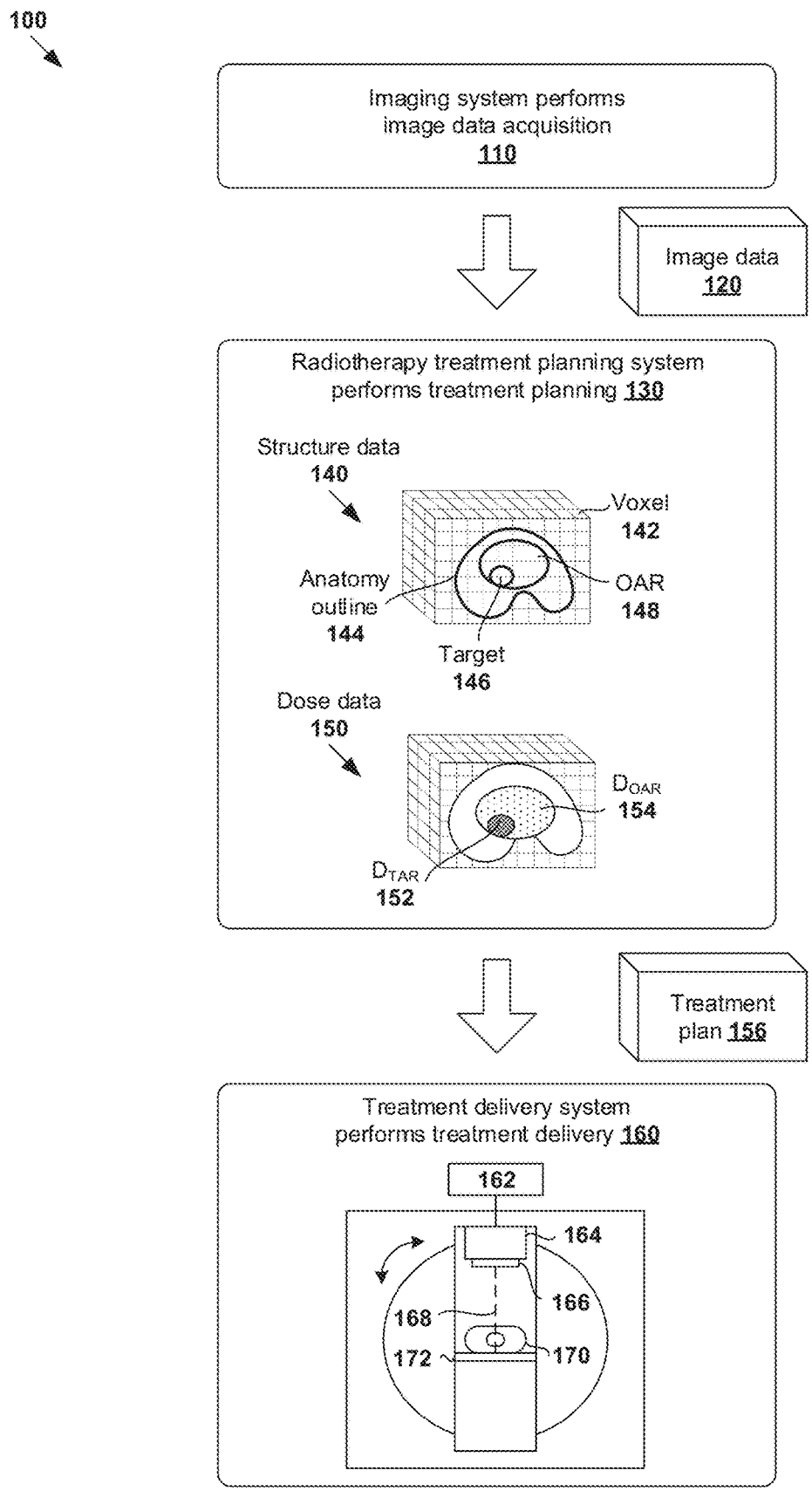
FIG. 1 is a schematic diagram illustrating an example process flow for radiotherapy treatment.

FIG. 1 is a schematic diagram illustrating example process flow 110 for radiotherapy treatment. Example process 110 may include one or more operations, functions, or actions illustrated by one or more blocks. The various blocks may be combined into fewer blocks, divided into additional blocks, and/or eliminated based upon the desired implementation. In the example in FIG. 1, radiotherapy treatment generally includes various stages, such as an imaging system performing image data acquisition for a patient (see 110); a radiotherapy treatment planning system (see 130) generating a suitable treatment plan (see 156) for the patient; and a treatment delivery system (see 160) delivering treatment according to the treatment plan.

In more detail, at 110 in FIG. 1, image data acquisition may be performed using an imaging system to capture image data 120 associated with a patient (particularly the patient's anatomy). Any suitable medical image modality or modalities may be used, such as computed tomography (CT), cone beam computed tomography (CBCT), positron emission tomography (PET), magnetic resonance imaging (MRI), magnetic resonance tomography (MRT), single photon emission computed tomography (SPECT), any combination thereof, etc. For example, when CT or MRI is used, image data 120 may include a series of two-dimensional (2D) images or slices, each representing a cross-sectional view of the patient's anatomy, or may include volumetric or three-dimensional (3D) images of the patient, or may include a time series of 2D or 3D images of the patient (e.g., four-dimensional (4D) CT or CBCT).

At 130 in FIG. 1, radiotherapy treatment planning may be performed during a planning phase to generate treatment plan 156 based on image data 120. Any suitable number of treatment planning tasks or steps may be performed, such as segmentation, dose prediction, projection data prediction, treatment plan generation, etc. For example, segmentation may be performed to generate structure data 140 identifying various segments or structures from image data 120. In practice, a three-dimensional (3D) volume of the patient's anatomy may be reconstructed from image data 120. The 3D volume that will be subjected to radiation is known as a treatment or irradiated volume that may be divided into multiple smaller volume-pixels (voxels) 142. Each voxel 142 represents a 3D element associated with location (i, j, k) within the treatment volume. Structure data 140 may be include any suitable data relating to the contour, shape, size and location of patient's anatomy 144, target 146, organ-at-risk (OAR) 148, or any other structure of interest (e.g., tissue, bone). For example, using image segmentation, a line may be drawn around a section of an image and labeled as target 146 (e.g., tagged with label="prostate"). Everything inside the line would be deemed as target 146, while everything outside would not.

In another example, dose prediction may be performed to generate dose data 150 specifying radiation dose to be delivered to target 146 (denoted "$D_{TAR}$" at 152) and radiation dose for OAR 148 (denoted "$D_{OAR}$" at 154). In practice, target 146 may represent a malignant tumor (e.g., prostate tumor) requiring radiotherapy treatment, and OAR 148 a proximal healthy structure or non-target structure (e.g., rectum, bladder) that might be adversely affected by the treatment. Target 146 is also known as a planning target volume (PTV). Although an example is shown in FIG. 1, the treatment volume may include multiple targets 146 and OARs 148 with complex shapes and sizes. Further, although shown as having a regular shape (e.g., cube), voxel 142 may have any suitable shape (e.g., non-regular). Depending on the desired implementation, radiotherapy treatment planning at block 130 may be performed based on any additional and/or alternative data, such as prescription, disease staging, biologic or radiomic data, genetic data, assay data, biopsy data, past treatment or medical history, any combination thereof, etc.

Based on structure data 140 and dose data 150, treatment plan 156 may be generated to include 2D fluence map data for a set of beam orientations or angles. Each fluence map specifies the intensity and shape (e.g., as determined by a multileaf collimator (MLC)) of a radiation beam emitted from a radiation source at a particular beam orientation and at a particular time. For example, in practice, intensity modulated radiotherapy treatment (IMRT) or any other treatment technique(s) may involve varying the shape and intensity of the radiation beam while at a constant gantry and couch angle. Alternatively or additionally, treatment plan 156 may include machine control point data (e.g., jaw and leaf positions), volumetric modulated arc therapy (VMAT) trajectory data for controlling a treatment delivery system, etc. In practice, block 130 may be performed based on goal doses prescribed by a clinician (e.g., oncologist, dosimetrist, or planner), such as based on the clinician's experience, the type and extent of the tumor, patient geometry and condition, etc.

At 160 in FIG. 1, treatment delivery is performed during a treatment phase to deliver radiation to the patient according to treatment plan 156. For example, radiotherapy treatment delivery system 160 may include rotatable gantry 164 to which radiation source 166 is attached. During treatment delivery, gantry 164 is rotated around patient 170 supported on structure 172 (e.g., table) to emit radiation beam 168 at various beam orientations according to treatment plan 156. Controller 162 may be used to retrieve treatment plan 156 and control gantry 164, radiation source 166 and radiation beam 168 to deliver radiotherapy treatment according to treatment plan 156.

It should be understood that any suitable radiotherapy treatment delivery system(s) may be used, such as mechanic-arm-based systems, tomotherapy type systems, brachy therapy, sirex spheres, any combination thereof, etc. Additionally, examples of the present disclosure may be applicable to particle delivery systems (e.g., proton, carbon ion). Such systems may employ either a scattered particle beam that is then shaped by a device akin to an MLC, or a scanning beam of adjustable energy, spot size and dwell time. Also, OAR segmentation might be performed, and automated segmentation of the applicators might be desirable.

Conventionally, radiotherapy treatment planning at block 130 in FIG. 1 is time and labor intensive. For example, it usually requires a team of highly skilled and trained oncologists and dosimetrists to manually delineate structures of interest by drawing contours or segmentations on image data 120. These structures are manually reviewed by a physician, possibly requiring adjustment or re-drawing. In many cases, the segmentation of critical organs can be the most time-consuming part of radiation treatment planning. After the structures are agreed upon, there are additional labor-intensive steps to process the structures to generate a clinically-optimal treatment plan specifying treatment delivery data such as beam orientations and trajectories, as well as corresponding 2D fluence maps. These steps are often complicated by a lack of consensus among different physicians and/or clinical regions as to what constitutes "good" contours or segmentation. In practice, there might be a huge variation in the way structures or segments are drawn by different clinical experts. The variation may result in uncertainty in target volume size and shape, as well as the exact proximity, size and shape of OARs that should receive minimal radiation dose. Even for a particular expert, there might be variation in the way segments are drawn on different days.

According to examples of the present disclosure, artificial intelligence (AI) techniques may be applied to ameliorate various challenges associated with radiotherapy treatment planning. In particular, deep learning engine(s) may be used to automate radiotherapy treatment planning task(s). Throughout the present disclosure, the term "deep learning" may refer generally to a class of approaches that utilizes many layers or stages of nonlinear data processing for feature learning as well as pattern analysis and/or classification. The "deep learning model" may refer to a hierarchy of "layers" of nonlinear data processing that include an input layer, an output layer, and multiple (i.e., two or more) "hidden" layers between the input and output layers. These layers may be trained from end-to-end (e.g., from the input layer to the output layer) to extract feature(s) from an input and classify the feature(s) to produce an output (e.g., classification label or class).

As used herein, the term "deep learning engine" may refer to any suitable hardware and/or software component(s) of a computer system that are capable of executing algorithms according to any suitable deep learning model(s). Depending on the desired implementation, any suitable deep learning model(s) may be used, such as convolutional neural network, recurrent neural network, deep belief network, generative adversarial network (GAN), or any combination thereof, etc. In practice, a neural network is generally formed using a network of processing elements (called "neurons," "nodes," etc.) that are interconnected via connections (called "synapses," "weights," etc.). For example, convolutional neural networks may be implemented using any suitable architecture(s), such as UNet, LeNet, AlexNet, ResNet, VNet, DenseNet, OctNet, any combination thereof, etc. A "processing layer" or "block" may be convolutional layer, pooling layer, un-pooling layer, rectified linear units (ReLU) layer, fully connected layer, loss layer, activation layer, dropout layer, transpose convolutional layer, concatenation layer, any combination thereof, etc.

Conventionally, there are many challenges associated with training deep learning engines for radiotherapy treatment planning. To achieve desirable training results, both the available training data as well as the training process are equally important. In practice, however, there are various challenges associated with training data gathering, curation and labeling. Even if some metrics are automatically estimated, the training data generally requires approval by a clinical expert. The lack of good quality training data may lead suboptimal results or, worse, failure to create any working deep learning engines, which is undesirable.

Training Boost for Deep Learning Engines

According to examples of the present disclosure, the training process of deep learning engines may be boosted to improve robustness and efficiency. In particular, the training process may be improved using a combination of labeled and unlabeled training data associated with radiotherapy treatment planning. This way, the training dataset may be expanded to reduce the risk of suboptimal training due to overlearning of features from a limited patient population, thereby improving robustness and efficiency. To further boost training, deep supervision may be implemented according to examples of the present disclosure. As used herein, the term "deep supervision" may refer generally to any suitable approach for providing supervision at hidden layer(s) of a deep learning engine, in addition to supervision at the final output layer.

Figure 2:
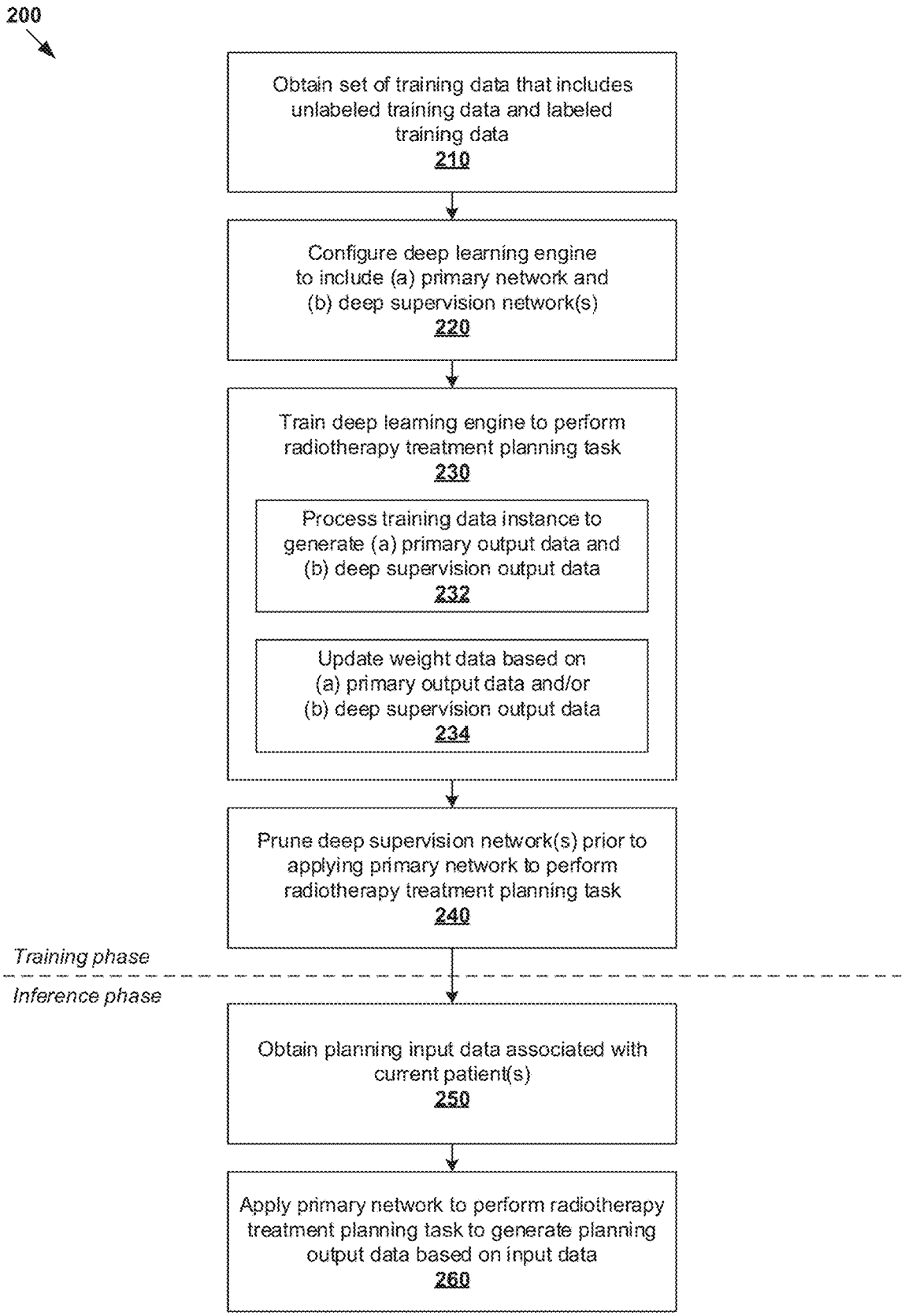
FIG. 2 is a flowchart of an example process for a computer system to train a deep learning engine for radiotherapy treatment planning.
Figure 9:
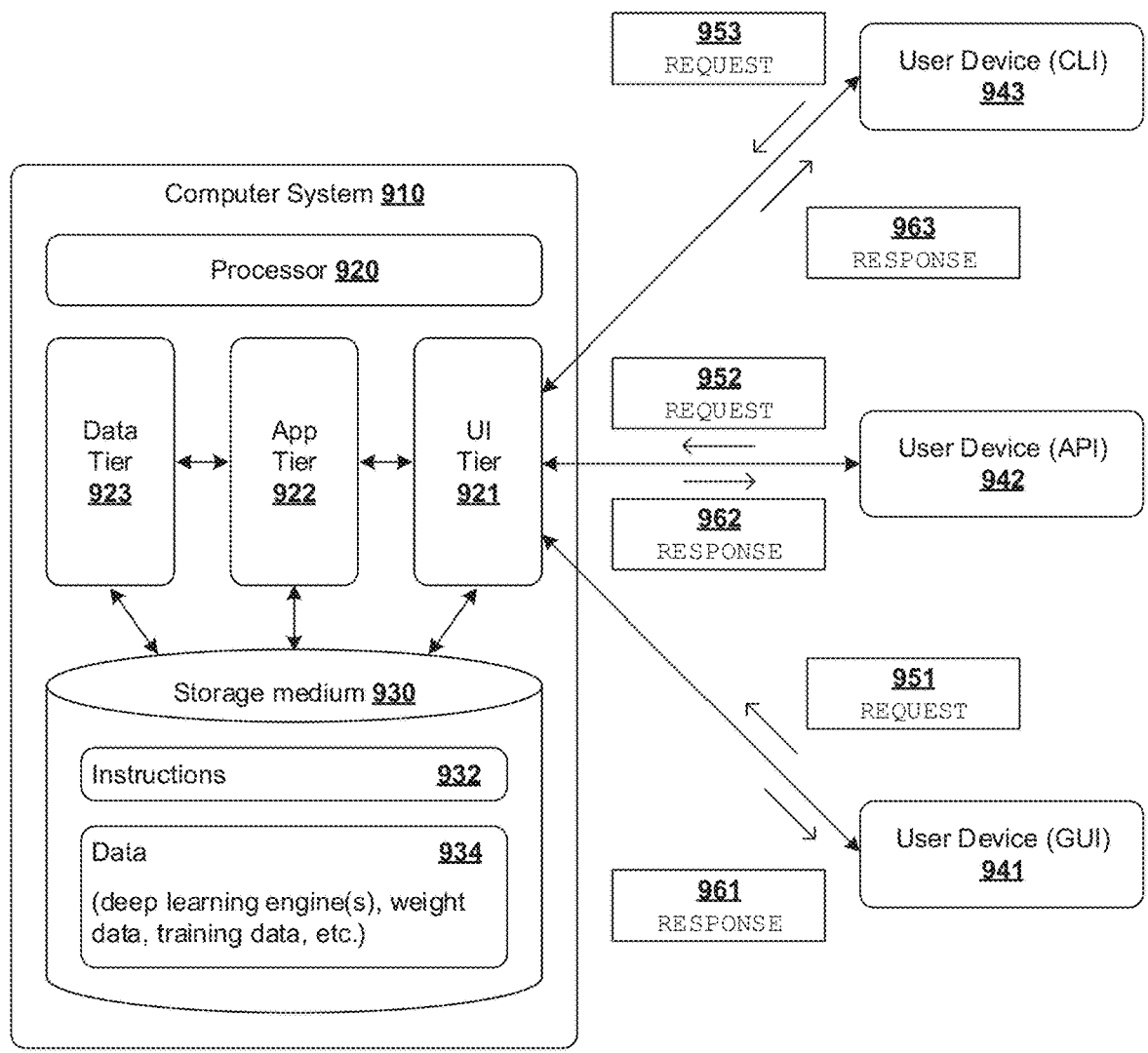
FIG. 9 is schematic diagram illustrating an example network environment in which radiotherapy treatment planning may be implemented.

In more detail, FIG. 2 is a flowchart of an example process 200 for a computer system to train a deep learning engine for radiotherapy treatment planning. Example process 200 may include one or more operations, functions, or actions illustrated by one or more blocks, such as 210 to 260. The various blocks may be combined into fewer blocks, divided into additional blocks, and/or eliminated based upon the desired implementation. The example in FIG. 2 will be explained using FIG. 3, which is a schematic diagram illustrating example deep learning engine 300 for radiotherapy treatment planning during a training phase. Examples of the present disclosure may be implemented using any suitable computer system(s), an example of which will be discussed using FIG. 9.

At 210 in FIG. 2, a set of training data that includes unlabeled training data (see 310 in FIG. 3) and labeled training data (see 320 in FIG. 3) associated with a radiotherapy treatment planning task may be obtained. Here, the term "obtain" may refer generally to a computer system receiving or retrieving data from any suitable source (e.g., another computer system), memory or datastore (e.g., local or remote), etc. The term "labeled" may refer generally to data whose label indicating desired output (e.g., segmentation) of radiotherapy treatment planning task is known. The term "unlabeled" may refer generally to data whose label is unknown.

At 220 in FIG. 2, deep learning engine 300 may be configured to include (a) a primary network and (b) one or more deep supervision networks. Here, the term "configure" may refer generally to any suitable operation(s) to implement deep learning engine 300 using a computer system, such as initialization of software object(s) representative of deep learning engine 300, assigning initial value(s) based on default or user-specified settings, etc. In the example in FIG. 3, block 220 may involve configuring primary network 301 that includes multiple processing layers in the form of input layer 330 (denoted as "IN"), multiple (N) hidden layers 331-334 (denoted as $L_i$, where i=1, ..., N) and output layer 335 (denoted as "OUT").

Block 220 may further involve configuring any suitable number (M) of deep supervision networks 340-350 (denoted as $D_j$, where j=1, ..., M) that branch off from primary network 301. For example, first deep supervision network ($D_1$) 340 may branch off primary network 301 at a first deep supervision checkpoint (see 341), and second deep supervision network 350 ($D_M$ for M=2) at a second deep supervision checkpoint (see 351). As used herein, the term "deep supervision network" may refer generally to a network of processing layers that branches off from a primary network (i.e., main pathway) of a deep learning engine to facilitate at supervision at hidden layer(s).

At 230 in FIG. 2, deep learning engine 300 may be trained to perform a radiotherapy treatment planning task based on training data 310-320. In particular, at 332, each training data instance may be processed to generate (a) primary output data 361 (denoted as X) using primary network 301 and (b) deep supervision output data 362/363 (denoted as $Y_j$, where 1≤j≤M) using deep supervision network 340/350. At 334, weight data associated with at least some of multiple processing layers 330-335 may be updated based on primary output data (X) 361 and/or deep supervision output data ($Y_j$) 362/363. The term "training data instance" may represent a subset of training data 310-320, such as a training case associated with a past patient.

Depending on the desired implementation, primary network 301 may represent a "task-specific" network that is trained to perform a radiotherapy treatment planning task. Deep supervision network ($D_j$, 1≤j≤M) may be attached to any suitable checkpoint along the task-specific network to make predictions of independent features based on deep feature(s) at that checkpoint, and propagate losses from that checkpoint backwards. For example, deep supervision output data 362/363 may identify anatomical feature(s) associated with the training data instance. By using both labeled and unlabeled training data 310-320, deep learning engine 300 may learn more general anatomical features. This should be contrasted against supervised learning, which might lead to overlearning from a limited patient population and lack of generalization to other patient populations.

At 240 in FIG. 2, deep supervision network 340/350 may be pruned from deep learning engine 301 prior to applying primary network 301 to perform the radiotherapy treatment planning task. This way, at 250-260, primary network 301 may be applied to perform the radiotherapy treatment planning task based on planning input data associated with current patient(s) to generate planning output data during a subsequent inference phase. Since primary network 301 is applied during inference phase, deep supervision network 340/350 may be pruned to reduce computational burden. In practice, deep supervision output data 362/363 may not be subject to clinical evaluation and therefore suffer from inaccuracies for the tracked metrics. In some cases, however, some metrics or features in deep supervision output data 362/363 may provide clinical information and be useful. In that case, the metrics may be documented, evaluated in a clinical setting and kept in the final model.

In practice, the selection of deep supervision feature(s) associated with deep supervision network 340/350 is generally non-trivial and may be guided by knowledge of what is problematic for deep learning engine 300 to learn. As will be described further using FIG. 5, deep supervision network 340/350 may generate deep supervision output data 362/363 identifying the following anatomical feature(s): distance to bone(s) or other bony landmark(s), distance to midline(s), distance to skin, presence of vertical and/or horizontal line(s), laterality, presence and classification of tumor site(s), orientation, anatomical region, presence of other segmented organ(s) or tagged landmark(s) that may not be related to the current task, any combination thereof, etc.

As will be discussed further using FIGS. 4-7, deep learning engine 300 may be trained to perform any suitable radiotherapy treatment planning task(s), such as automatic segmentation, dose prediction, treatment delivery data estimation, abnormal organ detection, treatment outcome prediction, any combination thereof, etc. In the case of automatic segmentation, engine 300 may be trained to generate planning output data=structure data (e.g., 140 in FIG. 1) based on planning input data=image data (e.g., 120 in FIG. 1). In the case of dose prediction, engine 300 may be trained to generate output=dose data (e.g., 150 in FIG. 1) based on input=image data, structure data or beam geometry data. In the case of treatment delivery data estimation, engine 210 may be trained to generate output=treatment delivery data (e.g., fluence map data, projection data) based on input=structure data and/or dose data, etc.

Automatic Segmentation

Figure 4:
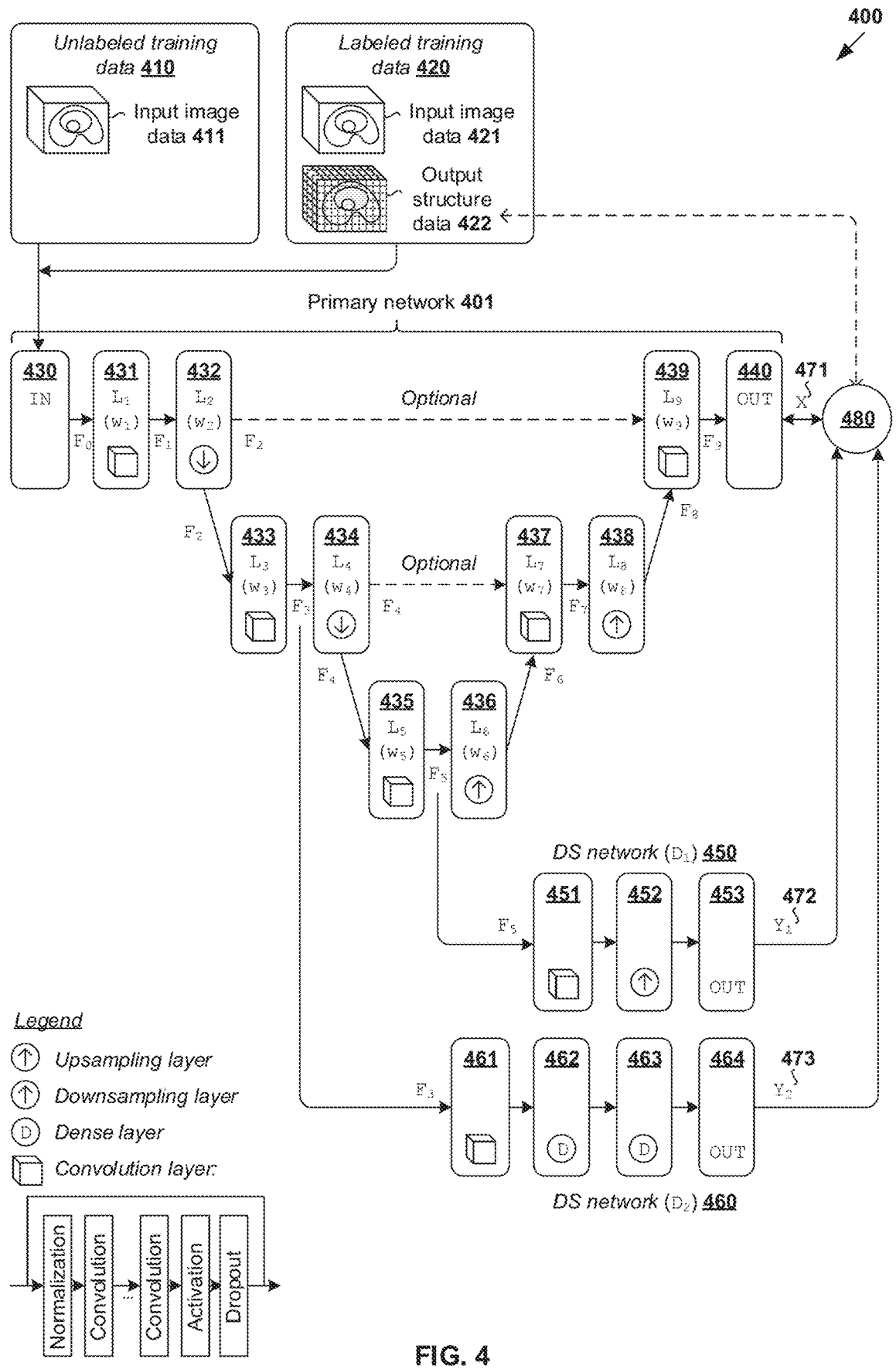
FIG. 4 is a schematic diagram illustrating an example deep learning engine for automatic segmentation during a training phase.
Figure 5:
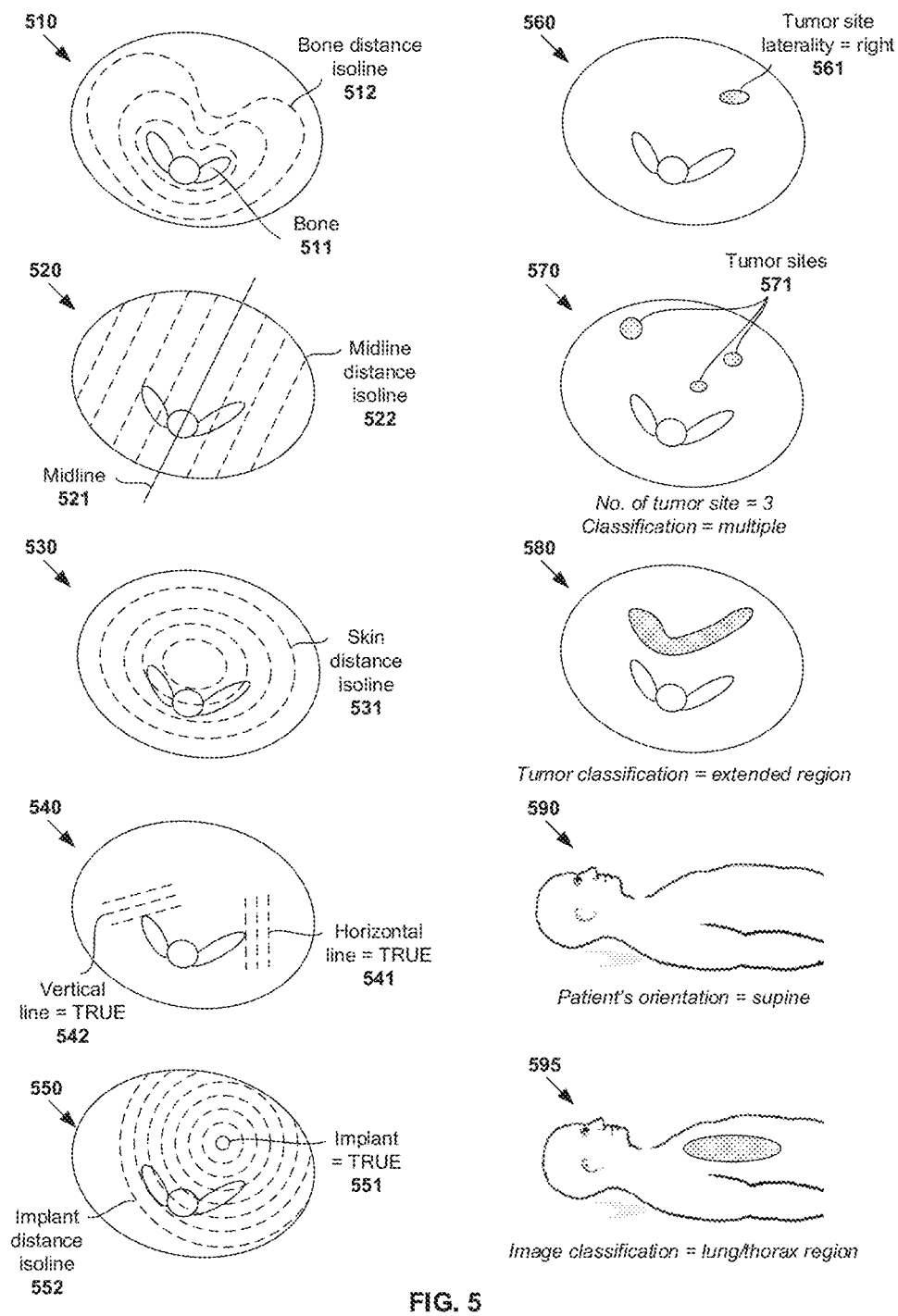
FIG. 5 is a schematic diagram illustrating example anatomical structures identifiable using deep supervision network(s)

Referring now to FIG. 4 and FIG. 5, training of a deep learning engine for automatic segmentation may be boosted according to examples of the present disclosure. In particular, FIG. 4 is a schematic diagram illustrating example deep learning engine 400 for automatic segmentation during a training phase. FIG. 5 is a schematic diagram illustrating example anatomical structures identifiable using deep supervision network(s). The result of deep learning engine 400 (also known as a "segmentation engine") may be used for subsequent radiotherapy planning tasks, such as abnormal organ detection, dose prediction, treatment delivery data estimation, etc.

(a) Training Data

At 410 and 420 in FIG. 4, labeled training data and unlabeled training data associated with past patients may be obtained from any suitable source(s), such as system provider, hospital, patient database, etc. Labeled training data 420 may include input training data=medical image data 421 and corresponding "labels" in the form of output training data=structure data 422. Labeled training data 420 may be denoted as $S_l=\{(x_1, \ldots, x_l), (y_1, \ldots, y_l)\}$, where $(x_1, \ldots, x_l)$ represents medical image data 421 for which structure data 422 denoted as $(y_1, \ldots, y_l)$ is known.

In contrast, unlabeled training data 410 may be denoted as $S_u=\{x_{l+1}, \ldots, x_{l+u}\}$ representing image data 411 with unknown labels. In practice, unlabeled training data 410 may include medical image data that is of good quality (e.g., as determined by clinicians). This way, the amount of training data may be expanded to facilitate semi-supervised learning, which is a combination of supervised and unsupervised learning. Unlabeled training data 410 may provide "additional information" for deep learning engine 400 to learn general rules about the human anatomy, etc.

Medical image data 411/421 may include 2D or 3D images of any suitable anatomical site(s) of patient's anatomy. The anatomical site may be generic for medical image data, or specific to a particular treatment. Structure data 422 may identify any suitable contour, shape, size and/or location of structure(s) identifiable from image data 421. Example structures may include target(s), OAR(s) or any other structure of interest (e.g., tissue, bone). In practice, a 3D volume of the patient that will be subjected to radiation is known as a treatment volume, which may be divided into multiple smaller volume-pixels (voxels). In this case, structure data 422 may specify a class label (e.g., "target" and "OAR") associated with each voxel in the 3D volume. Structure data 422 may identify multiple targets and OARs.

For example, in relation to prostate cancer, input image data 411/421 may show a patient's prostate region. In this case, structure data 422 may identify a target representing the patient's prostate, and OARs representing proximal healthy structures such as rectum and bladder. For lung cancer, image data 411/421 may be associated with a lung region. In this case, structure data 422 may identify target=cancerous lung tissue, and OAR(s)=proximal healthy lung tissue, esophagus, heart, etc. For brain cancer, image data 411/421 may show the brain region, and structure data 422 may identify target=brain tumor, and OAR(s)=proximal optic nerve, brain stem, etc. Training data 410/420 may be user-generated through experience and observations or extracted from past treatment plans developed for multiple past patients.

Structure data 422 may be associated with any suitable segmentation or contouring rules. Here, the term "rule" may refer to a clinical guideline, strategy and/or planning practice relating to a particular treatment planning task. For automatic segmentation, the rule(s) may specify when to stop contouring a structure superiorly and inferiorly, or whether the contour ends at the skin boundary or extends to the fat tissue. More advanced rule(s) may specify selection of the cutting plane of a structure (e.g., spinal cord), application of different margins at different sides of an organ (e.g., more margin inferior than superior sides of an organ), etc. In practice, training data 410-420 may be pre-processed using any suitable data augmentation approach to improve data quality, such as rotation, flipping, translation, scaling, noise addition, cropping, any combination thereof, etc.

Training data associated with multiple imaging modalities may be used, such as MRI, CT, PET, etc. In practice, unlabeled training data 410 may provide additional information that is useful for primary network 401 to learn general rules about patient anatomy. The additional information is only required during training phase. For example, MRI and CT image data may be used during training, but only CT image data during inference phase (to be discussed using FIG. 6). Depending on the desired implementation, labeled training data 420 may be intermixed with unlabeled training data 410 during training phase. Alternatively or additionally, unlabeled training data 410 may be used to prime primary network 401 during a pre-training phase before further training primary network 401 using labeled training data 420. In practice, the use of both labeled and unlabeled data during training may be referred generally as semi-supervised learning. Such semi-supervised approach is useful in scenarios where few labeled training data is available and/or it is relatively expensive to produce labeled training data (e.g., manually by clinicians).

(b) Primary Network

At 430-440 in FIG. 4, deep learning engine 400 may be configured to include primary network 401 for radiotherapy treatment planning. Primary network 401 may include an input layer (see 430), an output layer (see 440) and multiple (N) "hidden" processing layers (see 431-439) denoted as $L_i$ (i=1, \ldots, N). Any suitable deep learning model may be implemented, such as the example UNet-based architecture in FIG. 4 or any alternative architecture. In this case, primary network 401 may include a contracting path (left side) and an expansive path (right side). The contracting path includes repeated application of convolutions, followed by a ReLU layer and max pooling layer. Each step in the expansive path may include upsampling or transpose convolutions of the feature map followed by convolutions, etc.

In particular, primary network 401 may include convolution layers (see 431, 433, 435, 437, 439), downsampling layers (see 432, 434) and upsampling layers (see 436, 438) spread over three resolution levels. Referring to the legend in FIG. 4, each convolution layer may further include multiple blocks for normalization, convolution, activation, dropout, any combination thereof, etc. Referring to the dashed lines in FIG. 4, an optional copy of data from one processing layer may be transported to another to "skip" processing layer(s) in between. In one example, an optional copy of data from one processing layer ($L_2$) on the contracting path may be provided to another processing layer ($L_9$) on the expansive path. See corresponding 432 and 439, as well as 434 and 437.

Each $i^{th}$ processing layer ($L_i$) may be configured to extract feature data (denoted as $F_i$) from the output of a previous layer ($L_{i-1}$) based on associated weight data (denoted as $w_i$). At the start of the training phase, weight data ($w_i$) may be initialized to any suitable values. In one example, random values may be used for the weight data. In another example, deep transfer learning may be used to initialize weight data ($w_i$) during a pre-training process to further accelerate training phase. Depending on the desired implementation, each $i^{th}$ processing layer ($L_i$) may be configured to other operation(s) relating to activation functions, dropout, concatenations, batch normalizations, any combination thereof, etc.

In the case of i=1, first processing layer ($L_1$) 431 may process input feature data=$F_0$ from input layer 430 to generate output feature data=$F_1$ based on weight data ($w_1$) and. In the case of i=3, third processing layer ($L_3$) 433 may determine output feature data=$F_3$ based on weight data ($w_3$) and input feature data=$F_2$ from second layer 432. In the case of i=7, seventh processing layer ($L_7$) 437 may determine output=$F_7$ based on weight data ($w_7$) and inputs=($F_4$, $F_6$) generated by the respective fourth and sixth layers (see 434, 436). Here, the term "determine" or "process" may refer generally to any suitable operation(s) performed by a processing layer, such as convolution, upsampling, downsampling, normalization, activation, dropout, softmax classification, a combination thereof, etc. The output of primary network 401 is denoted as X (see 471).

(c) Deep Supervision Network(s)

At 450 and 460 in FIG. 4, deep learning engine 400 may be configured with multiple deep supervision networks (e.g., M=2). Each deep supervision network (denoted $D_j$) branches off from primary network 401 at a checkpoint that is interposed between two consecutive processing layers ($L_i$ and $L_{i+1}$). In the example in FIG. 4, first deep supervision network ($D_1$) 450 branches off from primary network 401 after processing layer ($L_5$) 435. Second deep supervision network ($D_2$) 450 branches off from primary network 401 after processing layer ($L_3$) 433.

Deep supervision networks 450-460 may be configured to provide direct supervision to "hidden" processing layers 431-438 of primary network 401. This should be contrasted against approaches of providing supervision only at output layer 440 of primary network 401 and subsequently propagating this supervision back to all earlier processing layers 431-439. Any suitable model may be used for each deep supervision network ($D_j$), such as neural network that is attached to any deep supervision checkpoint along primary network 401, etc. In practice, deep supervision network ($D_j$) should be relatively shallow so that the learning effect propagates to earlier layers in primary network 401.

The configuration of deep supervision network ($D_j$) may be task-dependent. For example, if the $j^{th}$ deep supervision task is to generate map data (e.g., distance map data), then corresponding deep supervision network ($D_j$) may include convolution and upsampling (deconvolution) blocks. If the deep supervision task is classification, then deep supervision network ($D_j$) may depend more on dense blocks. In the example in FIG. 4, first deep supervision network ($D_1$) 450 may include convolution block 451, upsampling block 452 and output block 453. Second deep supervision network ($D_2$) 460 may include convolution block 461, dense blocks 462-463 and output block 464. Output block 453/464 may be in the form of a softmax activation block, etc. Deep supervision outputs 472-473 of respective deep supervision networks 450-460 are denoted as $Y_1$ and $Y_2$.

(d) Primary and Deep Supervision Output Data

At 471-473 in FIG. 4, the training phase may involve determining primary output data (X) and deep supervision output data ($Y_1$, $Y_2$). In particular, primary network 401 may process a training data instance from training data 410/420 using processing layers 430-440 to generate primary loss (X); see 471. First deep supervision network 450 may process the training data instance to generate first deep supervision loss ($Y_1$), and second deep supervision network 460 to generate second deep supervision loss ($Y_2$); see 472-473.

Deep supervision networks 450-460 may be configured to estimate or predict deep supervision output data 472-473 representing anatomical features that are related to the automatic segmentation task in FIG. 4. This way, deep supervision output data 472-473 (also known as deep supervision losses) may be propagated backwards to improve earlier processing layers of primary network 401. This approach represents a mixture of transfer learning (where a network is trained to learn a related but independent task prior to task-specific training) and supervised learning (for task-specific training based on labeled training data 420).

Some deep supervision features are shown in FIG. 5, which is a schematic diagram illustrating example anatomical features identifiable using deep supervision networks 450-460. In the example in FIG. 5, deep supervision networks 450-460 may be configured to estimate the following features: distance to bone (see 510-512), distance to midline (see 520-522), distance to skin (see 530-531), presence of vertical and/or horizontal lines (see 540-542), distance to implant (see 550-552), tumor site laterality (see 560-561), presence of tumor sites (see 570-571), classification of tumor site(s) (see 580), patient's orientation (see 590), image classification identifying a particular anatomical region (see 595), any combination thereof, etc. The orientation may be legs- or head-first, supine/prone, etc.

Using deep supervision networks 450-460, anatomical feature(s) identifiable from training data 410-420 may be used to train primary network 401 in an unsupervised manner. The selection of deep supervision features is generally non-trivial and domain-specific. The selection of deep supervision features may be guided by expert knowledge of what is problematic for primary network 401 to learn. For example, if it is desirable to have primary network 401 to handle both prone and supine orientations, training data 410-420 should include both sufficient examples.

(e) Weight Data Update

At 480 in FIG. 4, a concatenation layer may be configured to determine a concatenated loss (Z) based on output data (X, $Y_1$, $Y_2$). Depending on the desired implementation, the concatenated loss (Z) may be calculated as a weighted combination of (X, $Y_1$, $Y_2$) based on corresponding weights ($\alpha, \beta_1, \beta_2$), as follows:

$$Z = \alpha X + \Sigma_{j=1}^{M} = \alpha X + \beta_1 Y_1 + \beta_2 Y_2.$$

Any suitable approach for weight distribution among output data 471-473 may be used. In practice, there are various challenges associated with feature selection and scheduling of deep supervision losses and the output loss, i.e., what is the balance between the loss from independent metrics estimated using deep supervision networks 450-460 or from the output loss from primary network 401. One example is to increase the weight for labeled training data 410 in stages in order to reduce the impact of unlabeled training data 410 over time. Another example is to increase the output weights ($\beta_1$, $\beta_2$) for deep supervision networks 450-460 "at points" to improve model generalization. This way, the output weights ($\beta_1, \beta_2$) may be increased during training so that the model does not get stuck on local minima and the final model would generalize as well as possible.

Depending on the desired implementation, all available losses (labeled and/or and unsupervised) may be concatenated. When labeled data is not available, that loss would not be used. This treatment of losses is readily available in deep learning training libraries, such as Keras (i.e., an open-source training library), etc. If labels are not available, setting the weight for X to zero (i.e., $\propto$=0) would achieve the same result in that there would be zero error to propagate through the network.

For labeled training data 410, a relatively simple loss function may be used, such as a mean squared error between a true outcome specified by output structure data 422 (i.e., desired outcome) and a predicted outcome. Alternatively, more complex loss functions may be used, such as dice loss, jaccard loss, focal loss, etc. The loss may be estimated at output layer 440, or any discrete point of primary network 401.

For unlabeled training data 410, there is no known label for corresponding input image data 411. In this case, deep supervision losses 472-473 may be generated by estimating independent feature(s). Each deep supervision loss ($Y_j$) may be propagated backwards from a particular checkpoint at which corresponding deep supervision network ($D_j$) branches off from primary network 401. This way, earlier layers of primary network 401 may learn relevant anatomical features from deep supervision networks 450-460 through backpropagation from those checkpoints. They also serve as a way to prime primary network 401 to handle the type of medical image data relevant for the radiotherapy treatment task=segmentation that primary network 401 is trained to perform.

In the case of j=1, first deep supervision network ($D_1$) 450 branches off from primary network 401 at a first checkpoint between processing layers ($L_5$, $L_6$) 435-436. As such, first deep supervision loss ($Y_1$) may be propagated backwards from the first checkpoint to update weight data=($w_1,w_2,w_3,w_4,w_5$) of subset=processing layers 431-435. In the case of j=2, second deep supervision network ($D_2$) 460 starts from a second checkpoint between processing layers ($L_3,L_4$) 433-434. As such, second deep supervision loss ($Y_2$) may be propagated backwards from that second checkpoint to weight data=($w_1,w_2,w_3$) of subset=processing layers 431-433. The above backpropagation process may be repeated until deep learning engine 400 is fully trained to achieve the desired outcome.

Dose Prediction and Other Planning Tasks

Figure 6:
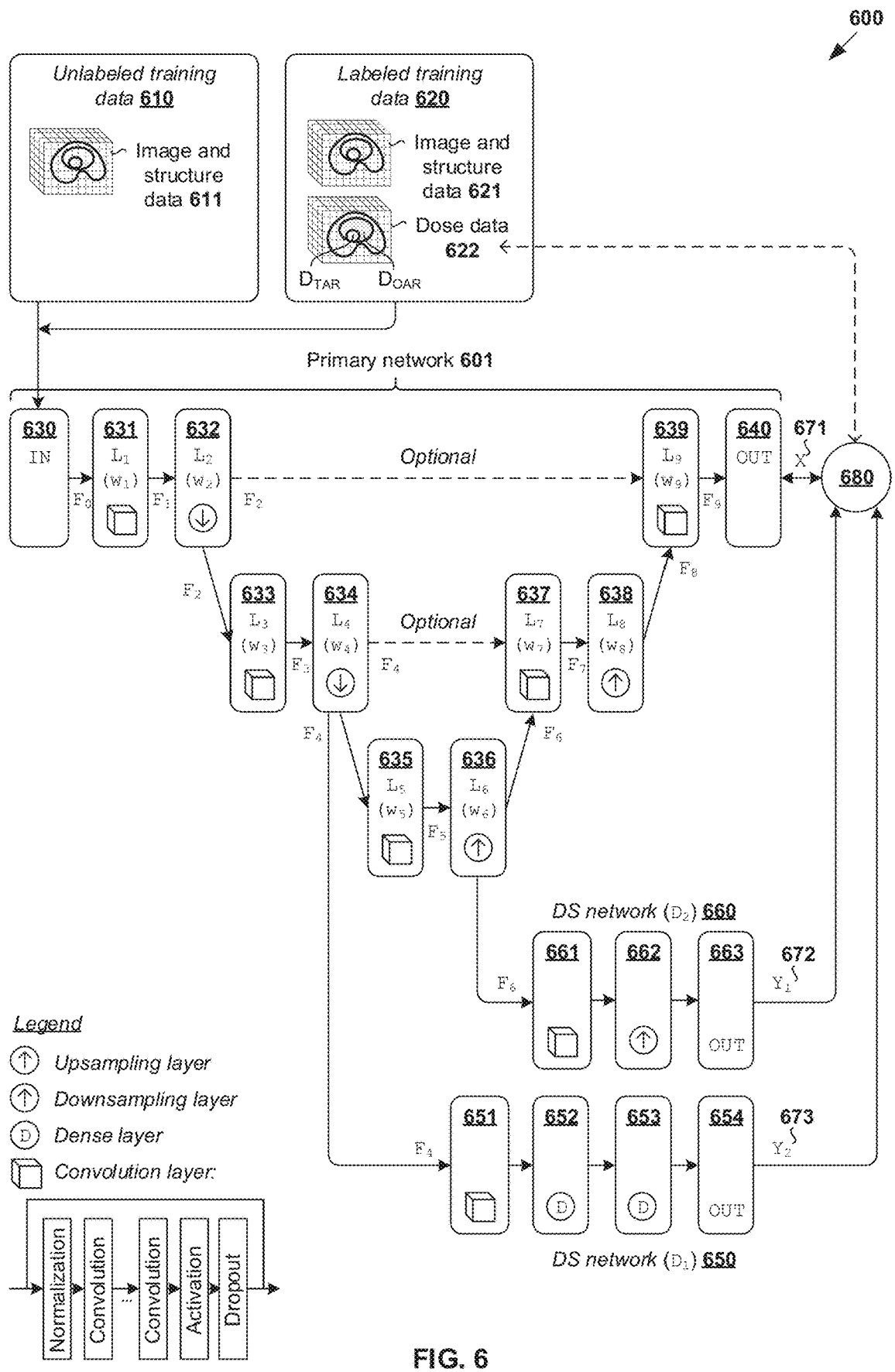
FIG. 6 is a schematic diagram illustrating an example deep learning engine for dose prediction during a training phase.

FIG. 6 is a schematic diagram illustrating example deep learning engine 600 for dose prediction during a training phase. In this example, deep learning engine 600 may be trained to perform dose prediction according to suitable constraint(s) may be used, such as limiting dose prediction to the vicinity of target(s) or certain dose levels. Note that various examples discussed using FIGS. 4-5 are also applicable to dose prediction in FIG. 6, and will not be repeated for brevity.

(a) Training Data

At 610 and 620 in FIG. 6, labeled training data and unlabeled training data associated with past patients may be obtained from any suitable source(s), such as system provider, hospital, patient database, etc. Unlabeled training data 610 may include image and/or structure data 611. Labeled training data 620 may include image and/or structure data 621, as well as known labels (i.e., desired outcome) in the form of dose data 622. Similar to the example in FIG. 4, unlabeled training data 610 may provide "additional information" to allow the deep learning engine to learn, for example, general rules about the human anatomy.

In practice, dose data 622 (e.g., 3D dose data) may specify dose distributions for a target (denoted "$D_{TAR}$") and an OAR (denoted "$D_{OAR}$"). For example, in relation to prostate cancer, dose data 622 may specify dose distributions for a target representing the patient's prostate, and an OAR representing a proximal healthy structure such as rectum or bladder. In practice, dose data 622 may specify the dose distributions for the whole 3D volume, not just the target and OAR volumes. Depending on the desired implementation, dose data 622 may include spatial biological effect data (e.g., fractionation corrected dose) and/or cover only part of the treatment volume. Besides structure data 621, additional input data may include beam geometry data associated with the treatment delivery system.

Dose data 622 may be generated using any suitable prediction rules, such as rules relating to organ sparing, target coverage (and dose prescription), and normal tissue dose. Additionally or alternatively, the prediction rule(s) may relate to treatment techniques (e.g., IMRT, VMAT), cancer type, machine specification (e.g., energy and field shape), or clinical practices for field placements. All these will have an impact on the predicted dose data. The prediction rule(s) may be learned implicitly from training data 620, or optionally provided as input parameters for certain types of deep learning engines.

(b) Primary and Deep Supervision Networks

At 630-640, deep learning engine 600 for dose prediction may be configured to include primary network 601. Similar to the example in FIG. 4, primary network 601 may include an input layer (see 630), an output layer (see 640) and multiple (N=9) "hidden" processing layers (see 631-639) denoted as $L_i$ (i=1, . . . , N). Any suitable deep learning model may be implemented, such as a UNet-based architecture in FIG. 6. In this case, primary network 601 may include convolution layers (see 631, 633, 635, 637, 639), downsampling layers (see 632, 634) and upsampling layers (see 636, 638).

At 650-660, deep learning engine 600 for dose prediction may be configured to include deep supervision networks denoted as $D_1$ and $D_2$. In the example in FIG. 6, first deep supervision network ($D_1$) 650 having with layers 651-654 branches off from primary network 601 at a first checkpoint after processing layer ($L_4$) 636. Second deep supervision network ($D_2$) 660 with layers 661-663 branches off from primary network 601 at a second checkpoint after processing layer ($L_6$) 636.

At 671-673 in FIG. 6, the training phase may involve determining a primary output data (X) and deep supervision output data ($Y_1$, $Y_2$). In particular, primary network 601 may process a training data instance from training data 610/620 using processing layers 630-640 to generate primary loss (X); see 671. First deep supervision network 650 may process the training data instance to generate first deep supervision loss ($Y_1$), and second deep supervision network 660 to generate second deep supervision loss ($Y_2$); see 672-673.

In one example, deep supervision networks 650-660 may be configured to estimate or predict deep supervision output data 672-673 representing anatomical features that are related to the dose prediction task in the example in FIG. 6. The examples in FIG. 5 are also applicable during dose prediction. In another example, deep supervision networks 650-660 may estimate or predict deep supervision output data 672-673 in the form of field placement, if the information is available. This task is usually highly interconnected to the anatomy of the patient, because the clinicians try to setup the fields to guide the treatment planning (i.e., treatment target, avoid critical organs). Other example deep supervision output data 672-673 may include prescription, number of fractions, photon/electron treatment, inclusion of a bolus during treatment, VMAT/IMRT treatment, any combination thereof, etc.

(c) Backpropagation

At 680 in FIG. 6, a concatenation layer may be configured to determine a concatenated loss (Z) based on output data (X, $Y_1$, $Y_2$). Depending on the desired implementation, the concatenated loss (Z) may be calculated as a weighted combination of (X, $Y_1$, $Y_2$) based on corresponding weights ($\propto$)$\beta_1$,$\beta_2$), such as $Z=\propto X+\Sigma_{j=1}\beta_j Y_j=\propto X+\beta_1 Y_1+\beta_2 Y_2$. Again, any suitable approach for weight distribution among output data 671-673 may be used. One example is to increase the weight for labeled training data 610 in stages in order to reduce the impact of unlabeled training data 620 over time.

For labeled training data 620, a relatively simple loss function may be used, such as a mean squared error between a true outcome specified by output structure data 622 (i.e., desired outcome) and a predicted outcome. Alternatively, more complex loss functions may be used. The loss may be estimated at output layer 640, or any discrete point of primary network 601. For unlabeled training data 610, there is no known label for input image data 611. In this case, deep supervision loss ($Y_j$) may be propagated backwards from a particular checkpoint at which deep supervision network ($D_j$) branches off from primary network 601.

In the case of j=1, first deep supervision network ($D_1$) 650 branches off from primary network 601 at a first checkpoint after processing layer. As such, first deep supervision loss ($Y_1$) may be propagated backwards from the first checkpoint to update weight data=($w_1,w_2,w_3,w_4,w_5,w_6$) of subset=processing layers 631-636. In the case of j=2, second deep supervision network ($D_2$) 660 starts from a second checkpoint after processing layer ($L_4$) 634. As such, second deep supervision loss ($Y_2$) may be propagated backwards from that second checkpoint to adjust weight data=. This way, earlier layers of primary network 601 may learn relevant anatomical features from deep supervision networks 650-660 through backpropagation from those checkpoints. The above backpropagation process may be repeated until deep learning engine 600 is fully trained to achieve the desired outcome.

Inference Phase

Figure 3:
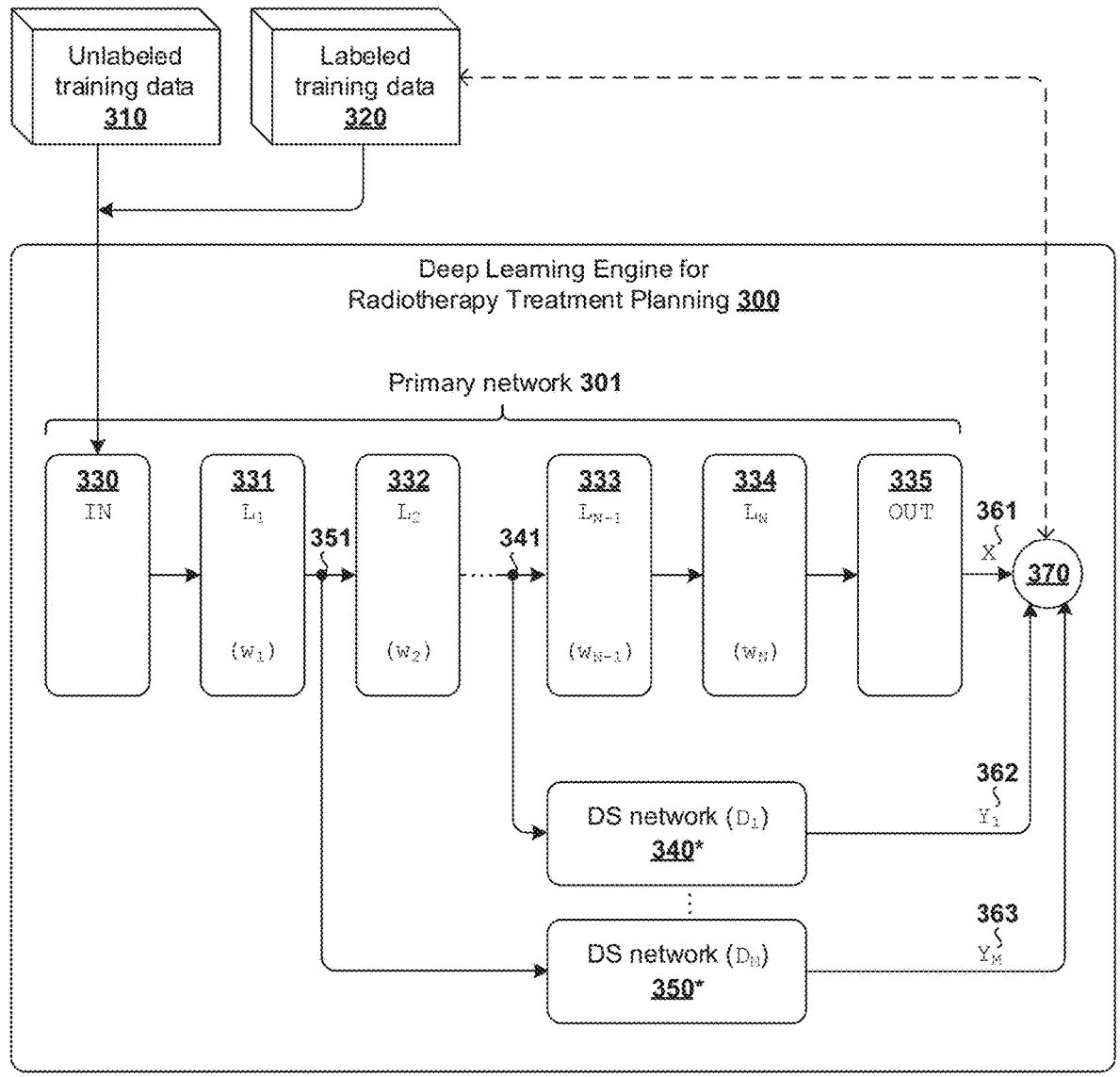
FIG. 3 is a schematic diagram illustrating an example deep learning engine for radiotherapy treatment planning during a training phase.
Figure 7:
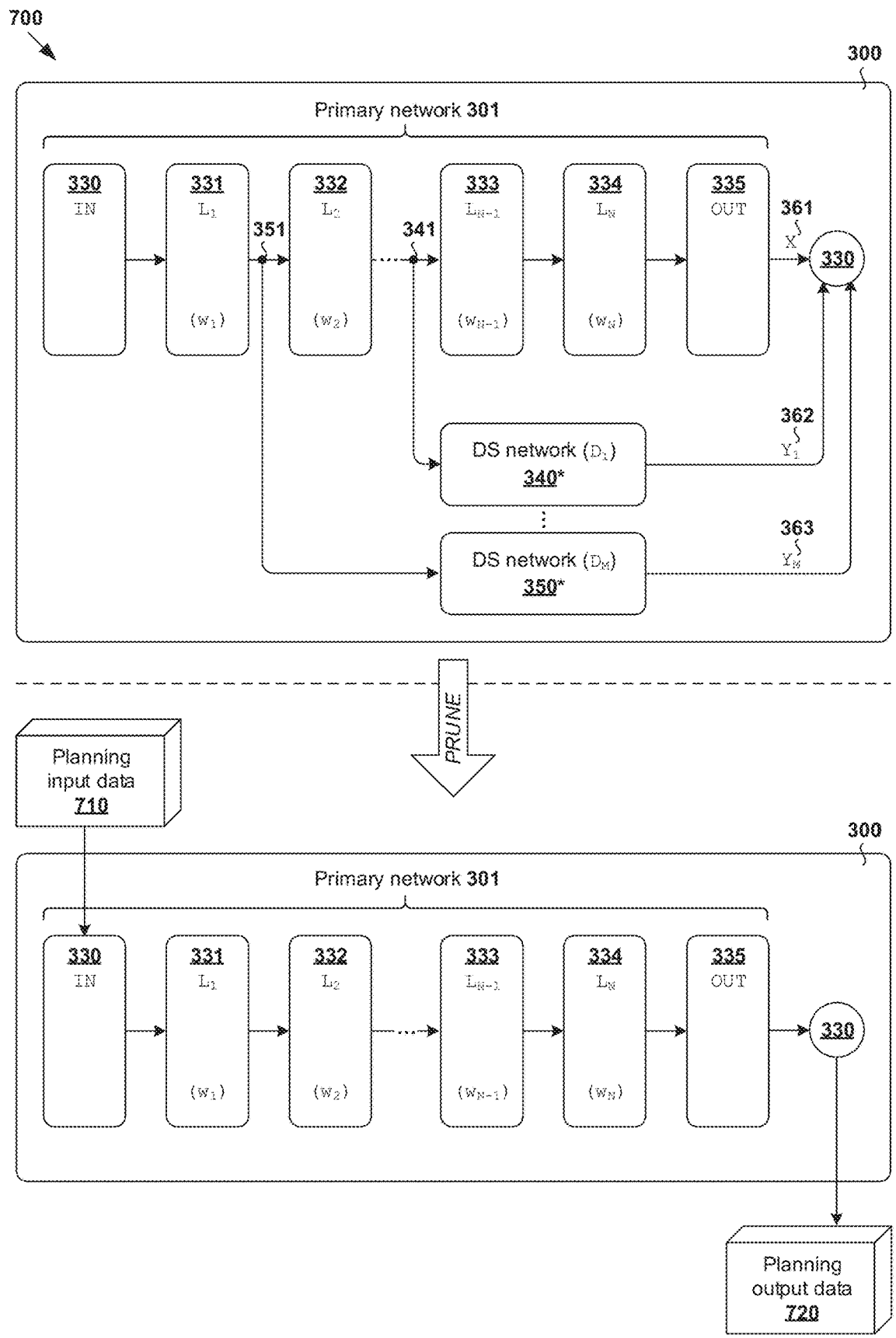
FIG. 7 is a schematic diagram illustrating the example deep learning engine for radiotherapy treatment planning in FIG. 3 during an inference phase.

FIG. 7 is a schematic diagram illustrating the example deep learning engine for radiotherapy treatment planning in FIG. 3 during inference phase 700. Once trained and validated, deep supervision networks 340-350 may be pruned or removed. This way, primary network 301 may be applied to perform radiotherapy treatment planning to generate planning output data 720 based on planning input data 710 associated with current patient(s). In practice, a "current patient" may be one of multiple patients who are being processed at the same time during inference phase 700. For example, automatic segmentation may be performed as image data is captured and transferred to a storage system, such as picture archiving and communication system (PACS), etc.

For the automatic segmentation example in FIG. 4, deep supervision networks 450-460 may be pruned. During subsequent inference phase, primary network 401 may be applied to perform automatic segmentation to generate planning output data=patient structure data 720 based on planning input data=image data 710 of current patient(s). For the dose prediction example in FIG. 6, deep supervision networks 650-660 may be pruned. During subsequent inference phase, primary network 601 may be applied to perform dose prediction to generate planning output data=dose data 720 based on planning input data=image data and/or structure data 710 of current patient(s).

Depending on the desired implementation, unlabeled training data 310 and labeled training data 320 may be intermixed to train deep learning engine 300 during the training phase in FIG. 3. Alternatively, unlabeled training data 310 may be used to train deep learning engine 300 during a pre-training, followed using labeled training data 320 for further training to achieve the desired training outcome. Further, unlabeled training data 310 and labeled training data 320 may include image data acquired using multiple imaging modalities (e.g., CT and MRI), but planning input data 710 may only include image data acquired using at least one of the imaging modalities (e.g., CT). In other words, CT and MRI images may be used during training but only CT images may be used during radiotherapy treatment planning.

Besides automatic segmentation and dose prediction, examples of the present disclosure may be implemented for other radiotherapy treatment planning tasks, such as treatment delivery data estimation, treatment outcome prediction, etc. In relation to treatment delivery data estimation, the estimated treatment delivery data (i.e., output data) may include structure projection data, fluence map data, etc. For example, a deep learning engine may be trained to perform structure projection data, such as based on image data, structure data, dose data, or any combination thereof. The structure projection data may include data relating to beam orientations and machine trajectories for a treatment delivery system.

In another example, examples of the present disclosure may be implemented to train a deep learning engine to perform fluence map estimation, such as 2D fluence maps for a set of beam orientations/trajectories, machine control point data (e.g., jaw and leaf positions, gantry and couch positions). Fluence maps will be explained further using FIG. 8. Any additional and/or alternative training data may be used, such as field geometry data, monitor units (amount of radiation counted by machine), quality of plan estimate (acceptable or not), daily dose prescription (output), field size or other machine parameters, couch positions parameters or isocenter position within patient, treatment strategy (use movement control mechanism or not, boost or no boost), treat or no treat decision.

In practice, medical image data generally includes both local and global feature data of a patient's anatomy, where the terms "local" and "global" are relative in nature. For example, the local feature data may provide a microscopic view of the patient's anatomy, such as tissue texture, whether a structure has a limiting border, etc. In contrast, the global feature data may provide a relatively macroscopic view of the patient's anatomy, such as which region the anatomy is located (e.g., prostate), orientation (e.g., to the left, to the right, front, back).

In practice, deep learning approaches should be contrasted against machine learning approaches that have been applied to, for example, automatic segmentation. In general, these approaches involve extracting (hand-designed) feature vectors from images, such as for every voxel, etc. Then, the feature vectors may be used as input to a machine learning model that classifies which class each voxel belongs to. However, such machine learning approaches usually do not make use of complete image data and additional constraints may be required. Another challenge is that these approaches rely on a high dimension of hand-designed features in order to accurately predict the class label for each voxel. Solving a high-dimensional classification problem is computationally expensive and requires a large amount of memory. Some approaches use lower dimensional features (e.g., using dimensionality reduction techniques) but they may decrease the prediction accuracy.

Example Treatment Plan

Figure 8:
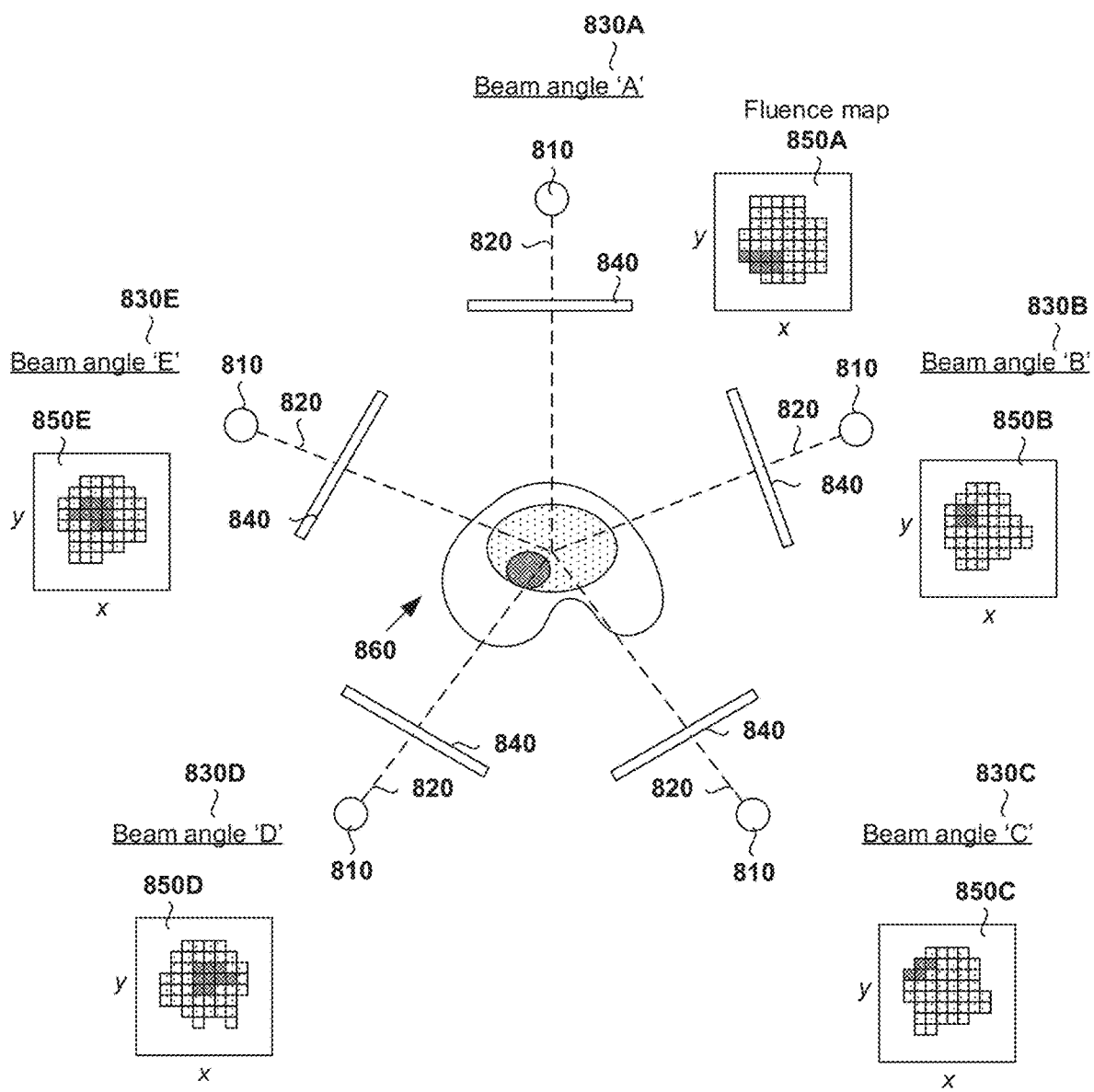
FIG. 8 is a schematic diagram of an example treatment plan generated or improved based on examples of the present disclosure.

FIG. 8 is a schematic diagram of an example treatment plan generated or improved based on examples of the present disclosure. Treatment plan 156 may be delivered using any suitable treatment delivery system that includes radiation source 810 to project radiation beam 820 onto treatment volume 860 representing the patient's anatomy at various beam angles 830. Although not shown in FIG. 8 for simplicity, radiation source 810 may include a linear accelerator to accelerate radiation beam 820 and a collimator (e.g., MLC) to modify or modulate radiation beam 820. In another example, radiation beam 820 may be modulated by scanning it across a target patient in a specific pattern with various energies and dwell times (e.g., as in proton therapy). A controller (e.g., computer system) may be used to control the operation of radiation source 820 according to treatment plan 156.

During treatment delivery, radiation source 810 may be rotatable using a gantry around a patient, or the patient may be rotated (as in some proton radiotherapy solutions) to emit radiation beam 820 at various beam orientations or angles relative to the patient. For example, five equally-spaced beam angles 830A-E (also labeled "A," "B," "C," "D" and "E") may be selected using a deep learning engine configured to perform treatment delivery data estimation. In practice, any suitable number of beam and/or table or chair angles 830 (e.g., five, seven) may be selected. At each beam angle, radiation beam 820 is associated with fluence plane 840 (also known as an intersection plane) situated outside the patient envelope along a beam axis extending from radiation source 810 to treatment volume 860. As shown in FIG. 8, fluence plane 840 is generally at a known distance from the isocenter.

In addition to beam angles 830A-E, fluence parameters of radiation beam 820 are required for treatment delivery. The term "fluence parameters" may refer generally to characteristics of radiation beam 820, such as its intensity profile as represented using fluence maps (e.g., 850A-E for corresponding beam angles 830A-E). Each fluence map (e.g., 850A) represents the intensity of radiation beam 820 at each point on fluence plane 840 at a particular beam angle (e.g., 830A). Treatment delivery may then be performed according to fluence maps 850A-E, such as using IMRT, etc. The radiation dose deposited according to fluence maps 850A-E should, as much as possible, correspond to the treatment plan generated according to examples of the present disclosure.

Computer System

Examples of the present disclosure may be deployed in any suitable manner, such as a standalone system, web-based planning-as-a-service (PaaS) system, etc. In the following, an example computer system (also known as a "planning system") will be described using FIG. 9, which is a schematic diagram illustrating example network environment 900 in which training and/or deployment of deep learning engine(s) may be implemented. Depending on the desired implementation, network environment 900 may include additional and/or alternative components than that shown in FIG. 9. Examples of the present disclosure may be implemented by hardware, software or firmware or a combination thereof.

Processor 920 is to perform processes described herein with reference to FIG. 1 to FIG. 8. Computer-readable storage medium 930 may store computer-readable instructions 932 which, in response to execution by processor 920, cause processor 920 to perform various processes described herein. Computer-readable storage medium 930 may further store any suitable data 934, such as data relating to deep learning engine(s), training data, weight data, primary output data, deep supervision output data, etc. In the example in FIG. 9, computer system 910 may be accessible by multiple user devices 941-943 via any suitable physical network (e.g., local area network, wide area network) In practice, user devices 941-943 may be operated by various users located at any suitable clinical site(s).

Computer system 910 may be implemented using a multi-tier architecture that includes web-based user interface (UI) tier 921, application tier 922, and data tier 923. UI tier 921 may be configured to provide any suitable interface(s) to interact with user devices 941-943, such as graphical user interface (GUI), command-line interface (CLI), application programming interface (API) calls, any combination thereof, etc. Application tier 922 may be configured to implement examples of the present disclosure. Data tier 923 may be configured to facilitate data access to and from storage medium 930. By interacting with UI tier 921, user devices 941-943 may generate and send respective service requests 951-953 for processing by computer system 910. In response, computer system 910 may perform examples of the present disclosure generate and send service responses 961-963 to respective user devices 941-943.

Depending on the desired implementation, computer system 910 may be deployed in a cloud computing environment, in which case multiple virtualized computing instances (e.g., virtual machines, containers) may be configured to implement various functionalities of tiers 921-923. The cloud computing environment may be supported by on premise cloud infrastructure, public cloud infrastructure, or a combination of both. Computer system 910 may be deployed in any suitable manner, including a service-type deployment in an on-premise cloud infrastructure, public cloud infrastructure, a combination thereof, etc. Computer system 910 may represent a computation cluster that includes multiple computer systems among which various functionalities are distributed. Computer system 910 may include any alternative and/or additional component(s) not shown in FIG. 9, such as graphics processing unit (GPU), message queues for communication, blob storage or databases, load balancer(s), specialized circuits, etc.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Throughout the present disclosure, the terms "first," "second," "third," etc. do not denote any order of importance, but are rather used to distinguish one element from another.

Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method for a computer system to train a deep learning engine for radiotherapy treatment planning, wherein the method comprises:
    obtaining a set of training data that includes unlabeled training data and labeled training data associated with a radiotherapy treatment planning task;
    configuring the deep learning engine to include (a) a primary network that includes multiple processing layers and (b) a deep supervision network that branches off from the primary network at a checkpoint that is interposed between two processing layers;
    training the deep learning engine to perform the radiotherapy treatment planning task by performing the following for each training data instance from the set of training data:
        processing the training data instance to generate (a) primary output data using the primary network and (b) deep supervision output data using the deep supervision network, wherein the deep supervision output data identifies one or more anatomical features associated with the training data instance; and
        updating weight data associated with at least some of the multiple processing layers based on the primary output data or the deep supervision output data, or both; and
    applying the primary network to perform the radiotherapy treatment planning task based on input image data acquired using a first imaging modality,
    wherein the set of training data includes labeled training image data acquired using the first imaging modality and unlabeled training image data acquired using a second imaging modality.

2. The method of claim 1, wherein training the deep learning engine comprises:
    based on deep supervision output data, updating the weight data associated with a subset of the multiple processing layers located prior to the checkpoint at which the deep supervision network branches off from the primary network.

3. The method of claim 2, wherein training the deep learning engine comprises:
    updating the weight data associated with the subset based on the deep supervision output data that identifies one or more of the following anatomical features:
        distance to bone or bony landmark, distance to midline, distance to skin, presence of vertical and/or horizontal line, laterality, presence and classification of tumor site, orientation, anatomical region and presence of segmented organ or tagged landmark.

4. The method of claim 1, wherein training the deep learning engine comprises:
    updating the weight data associated with at least some of the multiple processing layers based on a weighted combination of the primary output data and the deep supervision output data.

5. The method of claim 1, wherein training the deep learning engine comprises:
    training the deep learning engine using the unlabeled training data during a pre-training phase prior to training the deep learning engine using the labeled training data.

6. The method of claim 1, wherein the method further comprises:
    pruning the deep supervision network from the deep learning engine; and
    applying the primary network to perform one of the following radiotherapy treatment planning tasks: automatic segmentation to generate structure data identifying one or more anatomical structures of the patient; dose prediction to generate output dose data for delivery to the patient; and treatment delivery data estimation to generate treatment delivery data for a treatment delivery system.

7. The method of claim 1, wherein the first imaging modality comprises computed tomography and the second imaging modality comprises magnetic resonance imaging.

8. A non-transitory computer-readable storage medium that includes a set of instructions which, in response to execution by a processor of a computer system, cause the processor to perform a method for training a deep learning engine for radiotherapy treatment planning, wherein the method comprises:
    obtaining a set of training data that includes unlabeled training data and labeled training data associated with a radiotherapy treatment planning task;
    configuring the deep learning engine to include (a) a primary network that includes multiple processing layers and (b) a deep supervision network that branches off from the primary network at a checkpoint that is interposed between two processing layers;
    training the deep learning engine to perform the radiotherapy treatment planning task by performing the following for each training data instance from the set of training data:
        processing the training data instance to generate (a) primary output data using the primary network and (b) deep supervision output data using the deep supervision network, wherein the deep supervision output data identifies one or more anatomical features associated with the training data instance; and
        updating weight data associated with at least some of the multiple processing layers based on the primary output data or the deep supervision output data, or both; and
    applying the primary network to perform the radiotherapy treatment planning task based on input image data acquired using a first imaging modality,
    wherein the set of training data includes labeled training image data acquired using the first imaging modality and unlabeled training image data acquired using a second imaging modality.

9. The non-transitory computer-readable storage medium of claim 8, wherein training the deep learning engine comprises:
    based on deep supervision output data, updating the weight data associated with a subset of the multiple processing layers located prior to the checkpoint at which the deep supervision network branches off from the primary network.

10. The non-transitory computer-readable storage medium of claim 9, wherein training the deep learning engine comprises:
updating the weight data associated with the subset based on the deep supervision output data that identifies one or more of the following anatomical features:
distance to bone or bony landmark, distance to midline, distance to skin, presence of vertical and/or horizontal line, laterality, presence and classification of tumor site, orientation, anatomical region and presence of segmented organ or tagged landmark.

11. The non-transitory computer-readable storage medium of claim 8, wherein training the deep learning engine comprises:
updating the weight data associated with at least some of the multiple processing layers based on a weighted combination of the primary output data and the deep supervision output data.

12. The non-transitory computer-readable storage medium of claim 8, wherein training the deep learning engine comprises:
training the deep learning engine using the unlabeled training data during a pre-training phase prior to training the deep learning engine using the labeled training data.

13. The non-transitory computer-readable storage medium of claim 8, wherein the method further comprises:
pruning the deep supervision network from the deep learning engine; and
applying the primary network to perform one of the following radiotherapy treatment planning tasks: automatic segmentation to generate structure data identifying one or more anatomical structures of the patient; dose prediction to generate output dose data for delivery to the patient; and treatment delivery data estimation to generate treatment delivery data for a treatment delivery system.

14. A computer system configured to train a deep learning engine for radiotherapy treatment planning, wherein the computer system comprises: a processor and a non-transitory computer-readable medium having stored thereon instructions that, when executed by the processor, cause the processor to:
obtain a set of training data that includes unlabeled training data and labeled training data associated with a radiotherapy treatment planning task;
configure the deep learning engine to include (a) a primary network that includes multiple processing layers and (b) a deep supervision network that branches off from the primary network at a checkpoint that is interposed between two processing layers;
train the deep learning engine to perform the radiotherapy treatment planning task by performing the following for each training data instance from the set of training data:
process the training data instance to generate (a) primary output data using the primary network and (b) deep supervision output data using the deep supervision network, wherein the deep supervision output data identifies one or more anatomical features associated with the training data instance; and
update weight data associated with at least some of the multiple processing layers based on the primary output data or the deep supervision output data, or both; and
applying the primary network to perform the radiotherapy treatment planning task based on input image data acquired using a first imaging modality,
wherein the set of training data includes labeled training image data acquired using the first imaging modality and unlabeled training image data acquired using a second imaging modality.

15. The computer system of claim 14, wherein the instructions for training the deep learning engine cause the processor to:
based on deep supervision output data, update the weight data associated with a subset of the multiple processing layers located prior to the checkpoint at which the deep supervision network branches off from the primary network.

16. The computer system of claim 15, wherein the instructions for training the deep learning engine cause the processor to:
update the weight data associated with the subset based on the deep supervision output data that identifies one or more of the following anatomical features:
distance to bone or bony landmark, distance to midline, distance to skin, presence of vertical and/or horizontal line, laterality, presence and classification of tumor site, orientation, anatomical region and presence of segmented organ or tagged landmark.

17. The computer system of claim 14, wherein the instructions for training the deep learning engine cause the processor to:
update the weight data associated with at least some of the multiple processing layers based on a weighted combination of the primary output data and the deep supervision output data.

18. The computer system of claim 14, wherein the instructions further cause the processor to:
prune the deep supervision network from the deep learning engine; and
apply the primary network to perform of the following radiotherapy treatment planning tasks: automatic segmentation to generate structure data identifying one or more anatomical structures of the patient; dose prediction to generate output dose data for delivery to the patient; and treatment delivery data estimation to generate treatment delivery data for a treatment delivery system.

* * * * *